United States Patent [19]

Alpern et al.

[11] Patent Number: 5,034,611
[45] Date of Patent: Jul. 23, 1991

[54] METHOD FOR NON-DESTRUCTIVE IDENTIFICATION FOR ELECTRONIC INHOMOGENEITIES IN SEMICONDUCTOR LAYERS

[75] Inventors: Peter Alpern, Munich; Dominique Savignac, Ismaning; Stefan Wurm, Munich, all of Fed. Rep. of Germany

[73] Assignee: Siemens Aktiengesellschaft, Munich, Fed. Rep. of Germany

[21] Appl. No.: 560,228

[22] Filed: Jul. 10, 1990

Related U.S. Application Data

[63] Continuation of Ser. No. 372,532, Jun. 28, 1989, abandoned.

[30] Foreign Application Priority Data

Jul. 1, 1988 [DE] Fed. Rep. of Germany ....... 3822346

[51] Int. Cl.$^5$ .............................................. G01N 21/55
[52] U.S. Cl. .................................... 250/372; 250/358
[58] Field of Search ............................ 250/358.1, 372

[56] References Cited

U.S. PATENT DOCUMENTS

| | | | |
|---|---|---|---|
| 4,352,016 | 9/1982 | Duffy et al. | 250/358.1 |
| 4,511,800 | 4/1985 | Harbeke et al. | 250/372 |
| 4,652,757 | 3/1987 | Carver | 250/360.1 |

OTHER PUBLICATIONS

Jon Opsal et al., "Temporal Behavior of Modulated Optical Reflectance in Silicon", *J. Appl. Phys.* 61(1), (Jan. 1, 1987), pp. 240–248.
Smith et al., "Ion Implant Monitoring With Thermal Wave Technology", *Appl. Phys. Lett.* 47 (6), (Sep. 15, 1985), pp. 584–586.
Opsal et al., "Thermal and Plasma Wave Depth Profiling in Silicon", *Appl. Phys. Lett.* 47(5), (Sep. 1, 1985), pp. 498–500.
S. Wurm, "Modulierte Optische Reflektivitat".

*Primary Examiner*—Constantine Hannaher
*Attorney, Agent, or Firm*—Hill, Van Santen, Steadman & Simpson

[57] ABSTRACT

A semiconductor layer is irradiated with an intensity-modulated laser emission to induce a modulated optical reflectivity which is a valid measure for the density of the electronic inhomogeneities in the semiconductor layer. The use of a test laser beam having a wavelength in a range of 200–345 nm makes exact measurements possible in the entire range of application and is particularly enabling for identification of low and high implantation doses and the identification of residual damage in crystalline semiconductor layers.

7 Claims, 2 Drawing Sheets

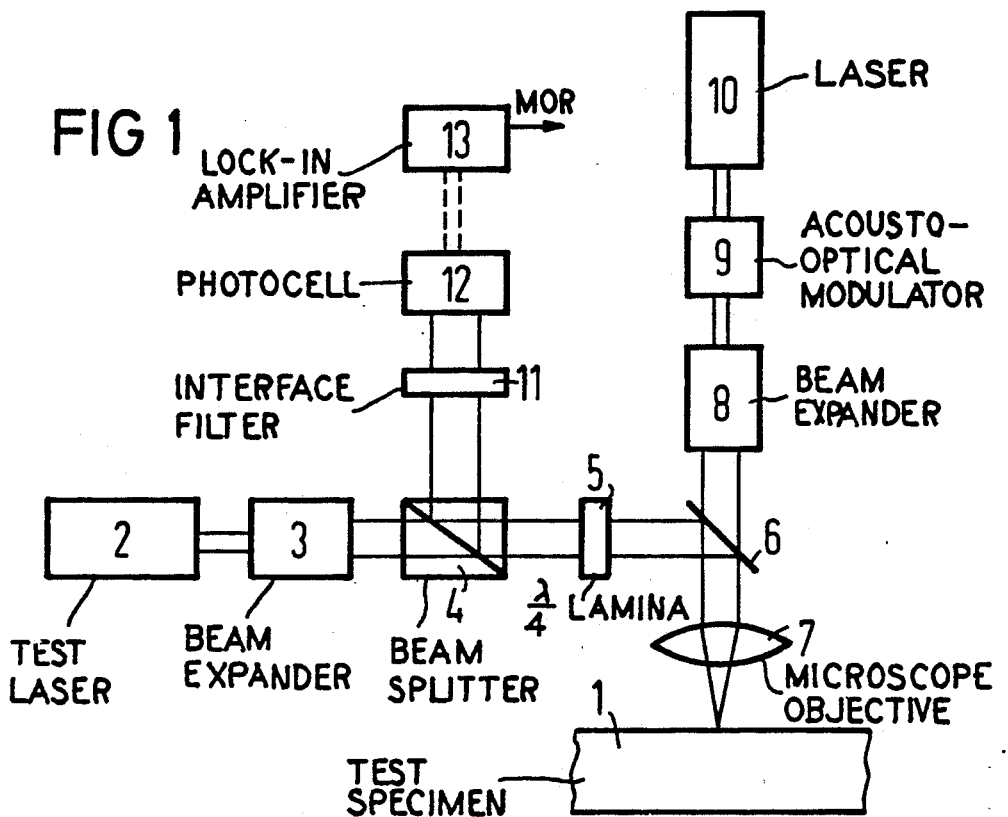
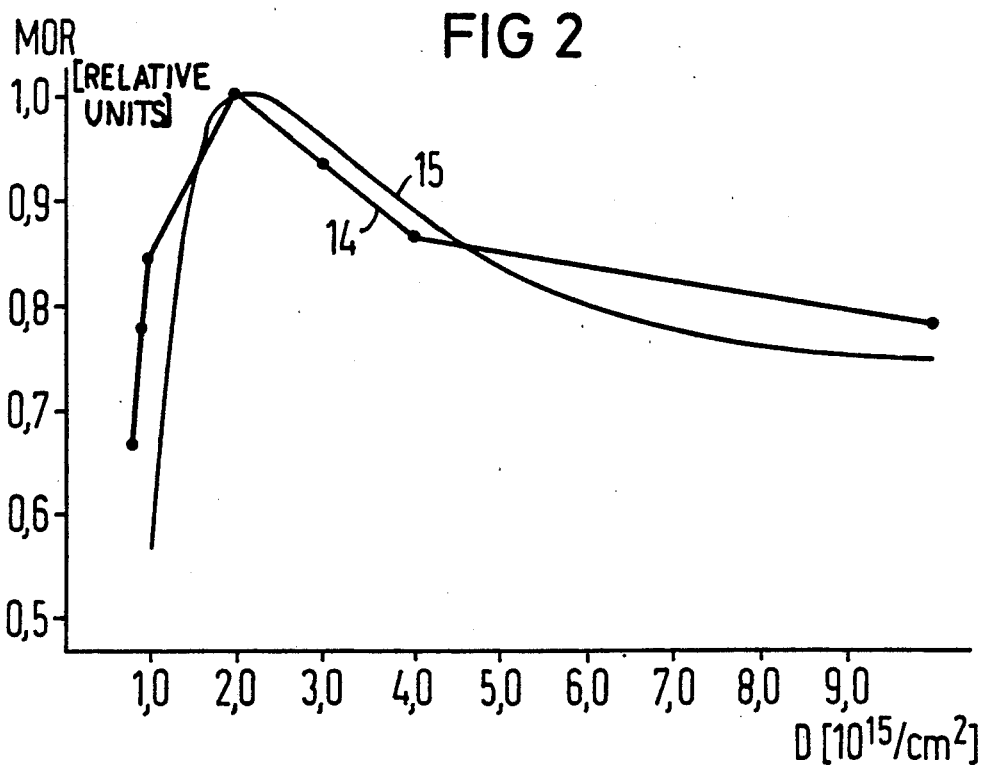

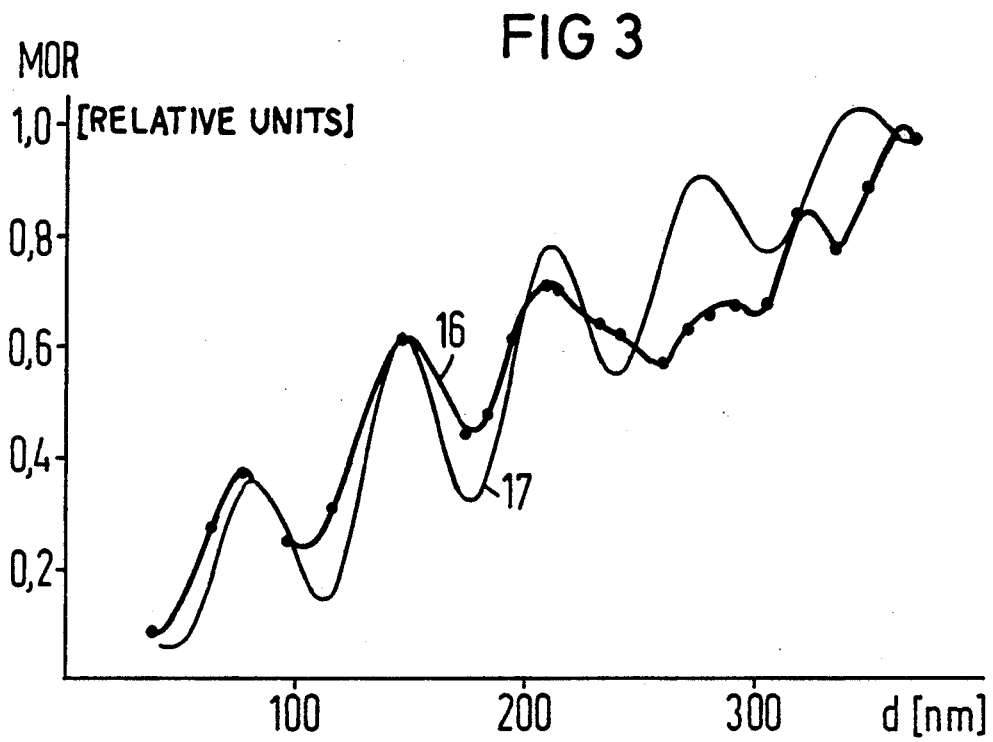
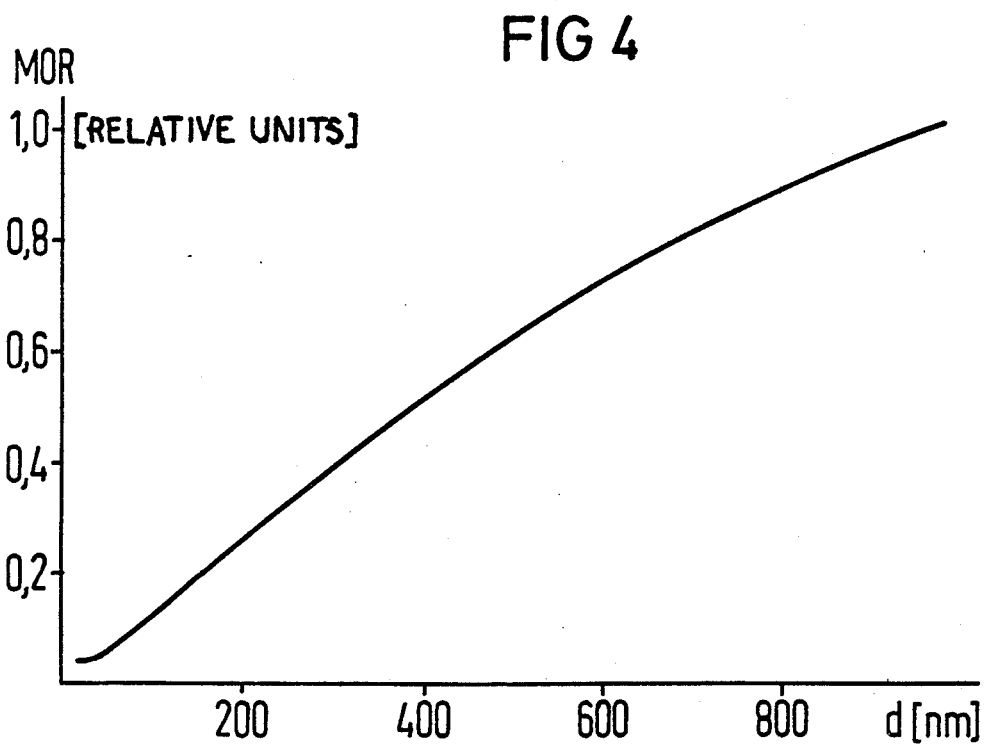

METHOD FOR NON-DESTRUCTIVE IDENTIFICATION FOR ELECTRONIC INHOMOGENEITIES IN SEMICONDUCTOR LAYERS

This is a continuation of application Ser. No. 372,532, filed June 28, 1989, abandoned.

BACKGROUND OF THE INVENTION

1. Field of the Invention

The present invention is directed generally to a method for non-destructive identification of electronic inhomogeneities in a semiconductor layer by measuring the modulated optical reflectivity that irradiation of the semiconductor layer with an intensity modulated laser radiation induces in a laser beam of a different wavelength.

2. Description of the Related Art

The need for and the demands made of non-destructive analysis methods for semiconductor layers increase with increasing miniaturization of the structures of semiconductor components. To monitor the individual process steps in the manufacture of semiconductor structures, optical measuring methods are used to identify electronic inhomogeneities that, for example, are produced by faults in the crystal and semiconductor layers or are due to ion implantations.

Optical measuring methods that utilize the effect known as modulated optical reflectivity, or the MOR technique, for identification of electronic inhomogeneities in a semiconductor layer are described in various publications, including *Applied Physics Letters*, 47 (6), 1985, pages 584–586; *Applied Physics Letters* 47 (5), 1985, pages 498–500; *Journal of Applied Physics* 61 (1), 1987, pages 240–248; and in a thesis by S. Wurm at the Technical University of Munich, Physics Department Institute E-13, April 1988. The modulated optical reflectivity technique is also used in commercially available measuring instruments such as the "Therma Probe 200" manufactured by Therma Wave Incorporated (USA).

Generally, the principle of measuring with modulated optical reflectivity will be described with reference to FIGS. 1 through 3. In FIG. 1, a functional block diagram of a measuring installation for identifying modulated optical reflectivity of a test specimen 1 is shown. An argon$^+$ ion laser 10, in the known embodiments, serves for the excitation of the test specimen 1 and, thus, operates as a pump laser. The argon$^+$ laser 10 produces a laser beam having a wavelength of approximately 488 nm at a power of approximately 5 mw, which is directed so that it is incident of the test specimen 1.

An acousto-optical modulator 9 is used to carry out intensity modulation of the argon beam at a prescribed modulation frequency of 1 MHz. The laser beam is focused onto the test specimen 1 using a beam expander 8 and a microscope objective 7.

A second laser 2 which is a helium-neon (HeNe) laser supplies a measuring laser beam of a wavelength of 632.8 nm at a power of between 2 to 3 mW. The helium-neon laser beam passes through a series of optical components, such as a second beam expander 3, a polarizing beam splitter 4, a quarter-wave lamina 5 and, with the assistance of a semi-reflective mirror 6, is coupled in through the microscope objective 7 parallel to the modulated argon$^+$ ion laser beam. The helium-neon beam is incident on the test specimen 1 confocally, i.e. collinearly, with the argon ion beam.

The helium-neon laser beam is reflected back by the test specimen 1 and again passes through the quarter-wave lamina 5 and the polarizing beam splitter 4, which steers the beam through an interface filter 11 onto a photocell 12 with which the test signal is detected. A lock-in amplifier 13 is connected at an output of the photocell 12. The lock-in amplifier 13 uses the modulation frequency (1 MHz.) of the argon$^+$ ion laser beam as a reference frequency and reproduces the amplitude of the specimen reflectivity for the helium-neon laser light periodically modulated with the frequency of 1 MHz as its output voltage. The output voltage is a modulated optical reflectivity signal MOR which is in arbitrary units. The MOR signal is proportional to the modification of the specimen reflectivity $\Delta R$ that derives as a difference between the reflectivity, or test signal, R occurring during excitation of the specimen by the pump laser 10 and the normal reflectivity $R_.$ occurring without excitation of the specimen by the pump laser 10, i.e. ($\Delta R = R - R_.$).

FIG. 2 is a graph of modulated optical reflectivity MOR as a function of implantation does D, also written as R(D). Shown in FIG. 2 is a first curve 14 depicting the dependency of the measured modulated optical reflectivity MOR for the helium-neon laser emission on the implantation dose D of an ion-implanted silicon layer. A second curve 15 on the graph of FIG. 2 is a plot of the calculated R(D) behavior obtained from a theoretical model. The illustrations of FIG. 2 are taken from the thesis by S. Wurm in which experimental work and theoretical considerations are set forth in greater detail.

In FIG. 3, a curve 16 shows the dependency of the measured modulated optical reflectivity MOR for the helium-neon laser emission as a function of thickness d of an amorphous silicon layer, in other words R(d). Test specimens of different thicknesses d were produced for the measurement by ion implantation of silicon$^+$ ions in crystal and silicon (100-material), whereby a constant implantation dose D of $1 \times 10^{15}$ ion/cm$^{-2}$ was observed and the implantation energy was varied. A second curve 17 on the graph of FIG. 3 reproduces the behavior obtained from a theoretical model for calculated values of R(D). Again, the illustrations of FIG. 3 are taken from the thesis of S. Wurm.

Identification of implantation doses in semiconductor layers by measuring the modulated optical reflectivity MOR with methods set forth above are suitable in a range of low implantation doses from about $10^{10}$ cm$^{-2}$ through $10^{13}$ cm$^{-2}$. In a range of high doses, above $10^{15}$ cm$^{-2}$, such as occur, for example, in source-drain implantations, an amorphous layer whose thickness depends both on the dose as well as on the implantation energy arises in the semiconductor surface. A layer system having different optical properties is thus present. No unambiguous allocation of the test signal to the implantation dose D is possible as a result of the interference effects due to reflection of the test laser beam in different layers. The test signal R is dependent on the layer thickness d of the implanted semiconductor layer, i.e. on the selected implantation energy, and thereby exhibits an oscillatory curve as shown in FIG. 3.

The implantation monitoring for a region of moderate implantation doses of from about $10^{13}$ cm$^{-2}$ through $10^{14}$ cm$^{-2}$ can be performed with film resistance measurements using contact probes. Up till now, though, there has been no alternative test procedures that can provide precise measured values for the range of high implantation doses.

An unambiguous allocation between the height of the test signal and the density of the faults is likewise not possible given use of the method for identifying residual damages, such as crystal faults, and crystalline semiconductor layers, since the test signal is dependent on the depth at which faults are situated in the semiconductor layer.

SUMMARY OF THE INVENTION

It is an object of the present invention to provide a method for non-destructive identification of electronic inhomogeneities in semiconductor layer with which the density of electronic inhomogeneities can be exactly identified. In particular, the present method is suitable for monitoring implantation in a region of high implantation doses, such as above $10^{15}$ cm$^{-2}$.

This and other objects of the invention are achieved by a method in which a laser emission having a wavelength in a range of from 200 through 345 nm is measured for the modulated optical reflectivity as a measure of the density of the electronic inhomogeneities.

A helium-neon (HeNe) laser beam has a wavelength of 632.8 nm and has a relatively great penetration depth into the semiconductor material because of its low absorption coefficient which is, for example, approximately 2000 nm in silicon. The penetration depth of a measuring laser beam into the silicon layer is greatly reduced when a laser emission in the wavelength of 200 through 345 nm is used, the penetration depth being approximately 10 nm in silicon at this range. This is true for the standard semiconductor materials such as, for example, silicon, germanium, gallium arsenide, gallium antimonide and indium phosphide which exhibits a great absorptivity at this wavelength. Contrary to the known methods, interference from the radiation of the measuring laser beam reflected from different depths of the semiconductor layer does not occur, so that an unambiguous relationship between the test signal and the density of the electronic inhomogeneities is obtained. It is thus possible to identify the electronic inhomogeneities present in the semiconductor layer with the method of the invention by measurement in the surface region of the semiconductor layer that is influenced by the electronic inhomogeneities.

Further developments and improvements of the invention include focusing the laser beam to be reflected so that a test spot having a diameter of approximately 0.5 through 5 micrometers arises in the semiconductor layer for the implementation of the topically resolved measurements. The present method can be also used for identification of the implantation dose in the semiconductor layers. In particular, it is useful for identifying the implantation dose in silicon layers. The method can be used to identify residual damage in crystalline semiconductor layers and in particular in silicon layers.

BRIEF DESCRIPTION OF THE DRAWINGS

FIG. 1 is a functional block diagram of an arrangement for measuring modulated optical reflectivity which illustrates the known method as well as the present invention;

FIG. 2 is a graph showing the dependency of the modulated optical reflectivity on implantation dose;

FIG. 3 is a graph showing the dependency of the modulated optical reflectivity on the thickness of a silicon layer; and FIG. 4 is a graph showing the dependency of the modulated optical reflectivity on the thickness of the layer for the present method.

DETAILED DESCRIPTION OF THE PREFERRED EMBODIMENTS

The measuring installation shown in FIG. 1 and described above is used as an exemplary embodiment for teaching the method of the present invention, where the following parameters are true. The pump laser 10 is an argon$^+$ ion laser having a wavelength of 488 nm and operating at a power of 5 mw. The test laser 2 is a helium-cadmium laser operating at a wavelength of 325 nm at a power of 8 mw. In an exemplary embodiment, the helium-cadmium laser is of a type multi-mode 356 XM, Omnichrom (Laser 200 Company, Munich). The microscope objective 7 is set so that the diameter of the test point on the specimen 1 is 1 micrometer and the penetration depth is 10 nm. The specimen 1 in the example is an implanted silicon layer with an implantation dose above approximately $10^{15}$ ions cm$^{-2}$.

In FIG. 4 is shown a graph of the anticipated dependency of the test signal of the modulated optical reflectivity MOR for the helium-cadmium laser emission over thickness d of the implanted silicon layer. The curve is calculated on the basis of the basic theoretical equations which are known in the prior art, for example, from the thesis of S. Wurm, whereby an amorphous silicon layer generated on a silicon substrate by ion-implantation with silicon$^+$ ions is utilized as the implanted silicon layer.

No interference effects whatsoever for thicknesses of greater that 20 nm are anticipated for the helium-cadmium laser emission due to the high co-efficient of absorption in silicon and in the ion-implanted silicon layer. The relationship between the modulated optical reflectivity R and the thickness d of the amorphous silicon layer shows an unambiguous allocation between the test signal and the implantation dose or implantation energy.

The method of the present invention is used for the entire, standard range of implantation doses and, in particular, is employed for structured semiconductor wafers. Given a test spot on the order of magnitude of 1 micrometer, the method of the invention is used for the implementation of topically resolved measurements.

The method of the invention is used for the analysis of any and all semiconductor layers wherein electronic inhomogeneities are present in characteristic fashion.

In addition to the use of the method for identifying implantation doses of semiconductor layers, the invention is particularly useful for identification of residual damage in crystalline semiconductor layers such as crystalline silicon layers.

Although other modifications and changes may be suggested by those skilled in the art, it is the intention of the inventors to embody within the patent warranted hereon all changes and modifications as reasonably and properly come within the scope of their contribution to the art.

We claim:

1. A method for non-destructive identification of electronic inhomogeneities of a semiconductor layer, comprising the steps of:
   irradiating a semiconductor layer with an intensity-modulated laser emission;
   directing a second laser emission onto the semiconductor layer for reflection, said second laser emission having a wavelength differing from a wavelength of said intensity-modulated laser emission, said second laser emission having a wavelength of approximately 200 through 345 nm; and measuring a modulated optical reflectivity of the semiconductor layer which is induced in said second laser emission as a measure of density of electronic inhomogeneities in the semiconductor layer.

2. A method as claimed in claim 1, further comprising the steps of:

focusing said second laser emission so that a test spot having a diameter of 0.5 through 5 micrometers arises on the semiconductor layer for implementing topically resolved measurements.

3. A method as claimed in claim 1, wherein said modulated optical reflectivity is used to identify an implantation dose in the semiconductor layer.

4. A method as claimed in claim 3, wherein said semiconductor layer is a silicon layer.

5. A method as claimed in claim 1, wherein said modulated optical reflectivity is used to identify residual damage in a crystalline semiconductor layer.

6. A method as claimed in claim 5, wherein said crystalline semiconductor layer is a crystalline silicon layer.

7. A method for non-destructive identification of electronic inhomogeneities in a semiconductor layer, comprising the steps of:

directing a modulated laser emission of a first wavelength onto a surface of a semiconductor layer;

directing a laser emission of a second wavelength in the range of approximately 200-345 nm onto the surface of the semiconductor layer at the same location as impinged by the modulated laser emission; and measuring the modulated optical reflectivity of the laser emission of the second wavelength to determine the density of the electronic inhomogeneities in the semiconductor layer.

* * * * *